US00PP28481P2

(12) United States Plant Patent
Li

(10) Patent No.: US PP28,481 P2
(45) Date of Patent: Oct. 3, 2017

(54) ***VERBENA* PLANT NAMED 'KLEVP15622'**

(50) Latin Name: *Verbena×hybrida*
Varietal Denomination: KLEVP15622

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 44 days.

(21) Appl. No.: 14/999,106

(22) Filed: Mar. 30, 2016

(51) Int. Cl.
*A01H 5/02* (2006.01)

(52) U.S. Cl.
USPC ..... Plt./308

(58) Field of Classification Search
USPC ..... Plt./263.1, 308
See application file for complete search history.

*Primary Examiner* — Susan McCormick Ewoldt
*Assistant Examiner* — Karen Redden
(74) *Attorney, Agent, or Firm* — Barbara Campbell; Bethany R. Roahrig; Cochran Freund & Young, LLC

(57) ABSTRACT

A new *Verbena* plant particularly distinguished by pink flowers with darker eyes, and a compact and upright growth habit, is disclosed.

1 Drawing Sheet

Genus and species: *Verbena×hybrida.*
Variety denomination: 'KLEVP15622'.

BACKGROUND OF THE NEW PLANT

The present invention comprises a new and distinct variety of *Verbena*, botanically known as *Verbena×hybrida*, and hereinafter referred to by the variety name 'KLEVP15622'. 'KLEVP15622' originated from a cross-pollination conducted in September 2012 in Cobbitty, New South Wales, Australia between the proprietary female *Verbena* variety '60.00.12' (unpatented), and the proprietary male *Verbena* variety '75.00.12' (unpatented).

The seeds from the cross were sown and plants were grown for evaluation, where an individual plant designated 'KLEVP15622' was selected from the group of plants in Cobbitty, New South Wales, Australia in October 2013.

In October 2013, 'KLEVP15622' was first vegetatively propagated by vegetative stem cuttings in Cobbitty, New South Wales, Australia. 'KLEVP15622' was found to reproduce true to type in successive generations of asexual propagation via vegetative stem cuttings.

SUMMARY

The following are the most outstanding and distinguishing characteristics of this new variety when grown under normal horticultural practices in Cobbitty, New South Wales, Australia.

1. Pink flowers with darker eyes; and
2. A compact and upright growth habit.

DESCRIPTION OF THE PHOTOGRAPH

This new *Verbena* plant is illustrated by the accompanying photograph which shows the plant's overall plant habit including form, foliage, and flowers. The photograph is of a 16-week-old plant grown in a greenhouse in Stuttgart, Germany in August 2014. The colors shown are as true as can be reasonably obtained by conventional photographic procedures.

DESCRIPTION OF THE NEW VARIETY

The following detailed descriptions set forth the distinctive characteristics of 'KLEVP15622'. The data which define these characteristics were collected from asexual reproductions carried out in Cobbitty, New South Wales, Australia. Data was collected on three-month-old plants grown in a greenhouse in Cobbitty, New South Wales, Australia in June 2015 in Cobbitty, New South Wales, Australia. Color references are to The R.H.S. Colour Chart of The Royal Horticultural Society of London (R.H.S.) 2007.

Classification:
- *Family.*—Verbenaceae.
- *Botanical.*—*Verbena×hybrida.*
- *Common.*—*Verbena.*
- *Designation.*—'KLEVP15622'.

Parentage:
- *Female parent.*—The proprietary female *verbena* variety '60.00.12' (unpatented).
- *Male parent.*—The proprietary male *verbena* variety '75.00.12' (unpatented).

Plant:
- *Growth habit.*—Compact and upright.
- *Height (from top of soil).*—32.0 cm.
- *Width (horizontal plant diameter).*—26.0 cm.
- *Time to produce a finished flowering plant.*—Approximately 8 weeks.
- *Time to initiate and develop roots.*—3 weeks.
- *Root description.*—RHS 155B (White); fine and fibrous roots.

Stems:
- *Number of branches per plant.*—More than 25.
- *Length.*—21.0 cm.
- *Diameter.*—0.25 cm.
- *Internode length.*—Approximately 1.8 cm.

*Color*.—RHS 130D.
*Anthocyanin*.—Absent.
*Texture and appearance*.—Pubescent, round.

Leaves:
*Arrangement*.—Opposite.
*Immature and mature leaf color*.—Upper surface: RHS 141A. Lower surface: RHS 141C.
*Length*.—2.3 cm.
*Width*.—1.4 cm.
*Shape*.—Lanceolate.
*Apex*.—Acute.
*Base*.—Obtuse.
*Margin*.—Crenate.
*Texture*.—Upper surface: Leathery. Lower surface: Rugose.
*Venation type*.—Pinnate.
*Venation color* (*both upper and lower surfaces*).—RHS 141D.
*Petioles*.—Length: 0.2 cm. Diameter: 0.1 cm. Color: RHS 141D. Texture: Leathery.

Flower buds:
*Shape*.—Tall, cylindrical.
*Length*.—0.6 cm.
*Diameter*.—0.2 cm.
*Color* (*at tight bud*).—RHS 50B.

Inflorescence:
*Blooming habit* (*flowering season*).—Continuously.
*Lastingness of individual blooms on the plant*.—6 to 10 days.
*Fragrance*.—Absent.
*Inflorescence type*.—Umbel.
*Length of inflorescence*.—5.9 cm.
*Diameter of inflorescence*.—5.9 cm.
*Number of florets per inflorescence*.—More than 20.
*Peduncle*.—Color: RHS 141A. Length: 1.0 cm. Diameter: 0.1 cm.

Florets:
*Length*.—2.0 cm.
*Diameter*.—1.5 cm.
*Texture*.—Glossy.
*Form*.—Single.
*Corolla tube length*.—1.2 cm.
*Corolla tube color* (*outer surface*).—RHS 155A.
*Petals*.—Length of lobe: 2.0 cm. Diameter of lobe: 2.5 cm. Lobe shape: Round. Apex: Acute. Base: Obtuse. Margin: Entire. Texture (both upper and lower surfaces): Glossy, satiny. Color: Immature: Upper surface: RHS 48C with RHS 51B eyes. Lower surface: RHS 38A. Mature: Upper surface: RHS 49A with RHS 52B eyes. Lower surface: RHS 38B.
*Pedicels*.—Not visible.

Sepals:
*Shape*.—Lanceolate.
*Apex*.—Acute.
*Base*.—Obtuse.
*Margin*.—Entire.
*Length*.—0.9 cm.
*Diameter*.—0.4 cm.
*Color*.—RHS 141C.
*Texture* (*both upper and lower surfaces*).—Hairy, dull.

Reproductive organs:
*Stamens*.—Present. Quantity: 4. Filament length: 0.5 cm. Filament diameter: 0.1 cm. Anther: Shape: Elliptic. Color: RHS 150B. Length: 0.7 cm. Diameter: 0.2 cm. Pollen amount: Sparse.
*Pistils*.—Number: 1. Length: 1.0 cm. Diameter: 0.1 cm. Stigma: Color: RHS 141D. Appearance: Ovate. Length: 0.1 cm. Diameter: 0.1 cm. Style: Color: RHS 140D. Length: 0.8 cm. Diameter: 0.1 cm. Appearance: Long.

Fruit and seed set: None observed.

Disease and pest/insect resistance: Good tolerance to powdery mildew (*Podosphaera xanthii*).

COMPARISON WITH PARENTAL LINES AND KNOWN VARIETY

'KLEVP15622' is distinguished from its parents as described in Table 1.

TABLE 1

Comparison with Parental Lines

| Characteristic | 'KLEVP15622' | Female parent '60.00.12' | Male parent '75.00.12' |
|---|---|---|---|
| Flower color | Pink with darker eyes | Pink | Pink |
| Branching —number of stems | More than 25 | 10 to 15 | 10 to 15 |

'KLEVP15622' is most similar to the commercial *verbena* 'VEAZ0006', also known commercially as LANAI 'Bright Pink' (U.S. Plant Pat. No. 23,508). Differences between the varieties are described in Table 2.

TABLE 2

Comparison with Similar Variety

| Characteristic | 'KLEVP15622' | 'VEAZ0006' |
|---|---|---|
| Growth habit | Compact and upright | Semi-mounding |
| Branching—number of stems | More than 25 | 10 to 15 |
| Eye color | Darker pink eyes | Tiny white eyes |

I claim:

1. A new and distinct variety of *Verbena* plant designated 'KLEVP15622' as illustrated and described herein.

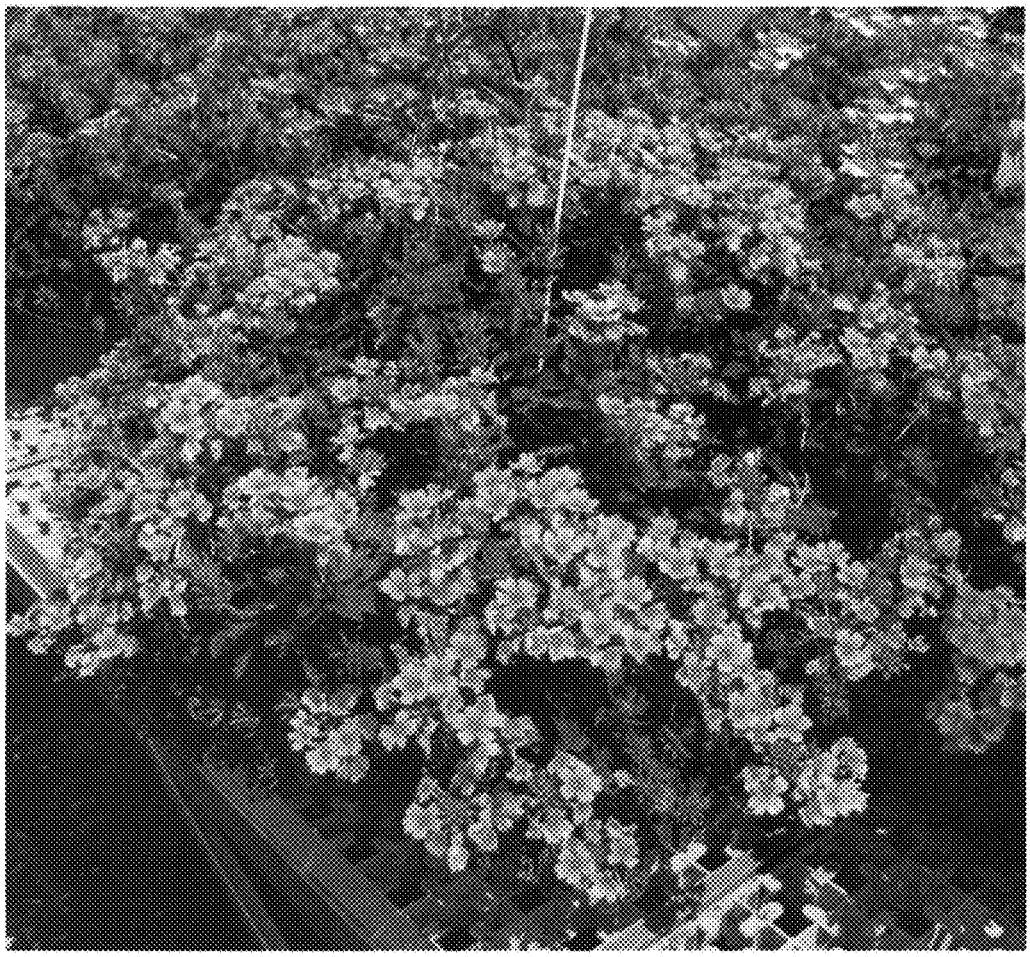

* * * * *